(12) United States Patent
Hatanaka et al.

(10) Patent No.: US 8,561,796 B2
(45) Date of Patent: Oct. 22, 2013

(54) PACKAGE MATERIAL FOR ADHESIVE BANDAGE AND PACKAGED ADHESIVE BANDAGE

(75) Inventors: Tomio Hatanaka, Tokyo (JP); Yumi Sumitani, Tokyo (JP)

(73) Assignee: Lintec Corporation, Tokyo (JP)

( * ) Notice: Subject to any disclaimer, the term of this patent is extended or adjusted under 35 U.S.C. 154(b) by 0 days.

(21) Appl. No.: 13/258,334

(22) PCT Filed: Mar. 16, 2010

(86) PCT No.: PCT/JP2010/054453
§ 371 (c)(1),
(2), (4) Date: Sep. 21, 2011

(87) PCT Pub. No.: WO2010/110130
PCT Pub. Date: Sep. 30, 2010

(65) Prior Publication Data
US 2012/0006710 A1    Jan. 12, 2012

(30) Foreign Application Priority Data
Mar. 24, 2009   (JP) .................................. 2009-072710

(51) Int. Cl.
*A61F 13/00* (2006.01)
*A61L 15/00* (2006.01)

(52) U.S. Cl.
USPC ................ 206/441; 206/440; 602/57; 602/41

(58) Field of Classification Search
USPC ........ 206/441, 440, 439, 460; 602/41, 42, 43, 602/54, 57
See application file for complete search history.

(56) References Cited

U.S. PATENT DOCUMENTS 3,313,405 A * 4/1967 Blackford ...................... 206/441
3,520,403 A * 7/1970 Moshel .......................... 206/441
(Continued)

FOREIGN PATENT DOCUMENTS

JP       09-150475 A    6/1997
JP      2002-502777 A   1/2002
(Continued)

OTHER PUBLICATIONS

International Search Report for International Application No. PCT/JP2010/054453, dated Jun. 22, 2010, 1 page.

*Primary Examiner* — J. Gregory Pickett
*Assistant Examiner* — Ernesto Grano
(74) *Attorney, Agent, or Firm* — Brinks Hofer Gilson & Lione

(57) ABSTRACT

Disclosed herein is a package material for adhesive bandage which is used for packaging therein an adhesive bandage including a surface base having one surface, an adhesive layer provided on the one surface of the surface base and a releasing sheet attached to the adhesive layer so as to cover it. The package material comprises a first sheet having a first sheet base and a first cold seal layer provided on the first sheet base, and a second sheet having a second sheet base and a second cold seal layer provided on the second sheet base. The first cold seal layer faces the surface base of the adhesive bandage and the second cold seal layer faces the releasing sheet of the adhesive bandage when the adhesive bandage is packaged in the package material. Further, each of the first cold seal layer and the second cold seal layer is formed of a mixture of rubber and acrylic resin, and an amount of the rubber contained in the first cold seal layer is smaller than an amount of the rubber contained in the second cold seal layer.

13 Claims, 2 Drawing Sheets

(56) References Cited

U.S. PATENT DOCUMENTS

| | | | |
|---|---|---|---|
| 4,182,449 A * | 1/1980 | Kozlow | 206/441 |
| 4,265,234 A * | 5/1981 | Schaar | 602/57 |
| 4,334,530 A * | 6/1982 | Hassell | 602/42 |
| 4,666,040 A * | 5/1987 | Murata | 206/441 |
| 4,972,829 A * | 11/1990 | Knerr | 602/52 |
| 5,099,832 A * | 3/1992 | Ward | 602/57 |
| 6,018,092 A * | 1/2000 | Dunshee | 602/54 |
| 6,099,682 A | 8/2000 | Krampe et al. | |
| 6,124,522 A | 9/2000 | Schroeder | |
| 6,225,522 B1 | 5/2001 | Schroeder | |
| 6,290,801 B1 | 9/2001 | Krampe et al. | |
| 6,436,499 B1 | 8/2002 | Krampe et al. | |
| 6,923,320 B2 * | 8/2005 | Grossman | 206/440 |
| 7,223,899 B2 * | 5/2007 | Sigurjonsson | 602/46 |
| 7,506,760 B2 * | 3/2009 | Grossman | 206/440 |
| 7,521,586 B2 | 4/2009 | Schroeder | |
| 7,659,439 B2 * | 2/2010 | Grossman | 602/57 |
| 2002/0064619 A1 | 5/2002 | Schroeder | |
| 2005/0181205 A1 * | 8/2005 | Story | 428/356 |
| 2007/0065620 A1 * | 3/2007 | Nonaka et al. | 428/40.1 |

FOREIGN PATENT DOCUMENTS

| | | |
|---|---|---|
| JP | 2002-530150 A | 9/2002 |
| JP | 2003-024369 A | 1/2003 |
| JP | 2009-022750 A | 2/2009 |
| WO | WO 2007/079071 A1 | 7/2007 |

* cited by examiner

PACKAGE MATERIAL FOR ADHESIVE BANDAGE AND PACKAGED ADHESIVE BANDAGE

TECHNICAL FIELD

The present invention relates to a package material for adhesive bandage and a packaged adhesive bandage.

RELATED ART

Conventionally, there is known a package material used for packaging therein an adhesive bandage which includes a surface base, an adhesive layer, a pad layer and a releasing sheet. This package material is composed of a pair of sheets each having a sheet base and a cold seal layer formed on a surface of the sheet base. The cold sheet layer is formed of rubber and acrylic resin (see, for example, Patent Document 1).

In such a package material, when the cold seal layers of the pair of sheets make contact with each other and then pressure is applied thereto, the cold seal layers are bonded together. By using such a property, the sheets are bonded together with the adhesive bandage being hermetically sealed in the package material. This makes it possible to prevent the adhesive bandage from being polluted with bacteria and the like.

However, in the case where a conventional package material is stored for a long period of time in a state that an adhesive bandage is packaged therein, there is a problem in that the cold seal layer of the sheet placed on the side of the surface base closely adheres (is bonded) to the surface base over time so that it becomes difficult to separate the adhesive bandage from the package material. In order to solve the above problem, it may be conceived to provide no cold seal layer in the sheet placed on the side of the surface base.

In such a case, the adhesive bandage is packaged in the package material in a state that the cold seal layer of the sheet placed on a side of the releasing sheet is bonded to the sheet base of the sheet placed on the side of the surface base. This causes another problem in that a sealing property of the package material cannot be kept. If such a sealing property of the package material is lowered, bacteria and the like infiltrate into the package material from a part thereof incompletely sealed so that the adhesive bandage is polluted. Namely, it is impossible to ensure a sterile condition of the adhesive bandage.

The Patent Document 1 is JP-A 09-150475.

SUMMARY OF THE INVENTION

It is an object of the present invention to provide an improved package material for adhesive bandage and a packaged adhesive bandage using the package material.

In order to achieve such an object, the present invention includes the following features (1) to (7).

(1) A package material for adhesive bandage which is adapted to be used for packaging an adhesive bandage therein, the adhesive bandage including a surface base having one surface, an adhesive layer provided on the one surface of the surface base and a releasing sheet attached to the adhesive layer so as to cover it, the package material for adhesive bandage comprising: a first sheet having a first sheet base and a first cold seal layer provided on the first sheet base; and a second sheet having a second sheet base and a second cold seal layer provided on the second sheet base, wherein the first cold seal layer faces the surface base of the adhesive bandage and the second cold seal layer faces the releasing sheet of the adhesive bandage when the adhesive bandage is packaged in the package material for adhesive bandage, and wherein each of the first cold seal layer and the second cold seal layer is formed of a mixture of rubber and acrylic resin, and an amount of the rubber contained in the first cold seal layer is smaller than an amount of the rubber contained in the second cold seal layer.

(2) In the package material for adhesive bandage described in the above-mentioned item (1), in the case where the amount of the rubber contained in the first cold seal layer is defined as A (mass %) and the amount of the rubber contained in the second cold seal layer is defined as B (mass %), A and B satisfy a relation of $1.05 \leq B/A \leq 2.40$.

(3) In the package material for adhesive bandage described in the above-mentioned item (1), in the first cold seal layer, a mass ratio of the rubber to the acrylic resin is in the range of 0.3:1 to 2.2:1.

(4) In the package material for adhesive bandage described in the above-mentioned item (1), in the second cold seal layer, a mass ratio of the rubber to the acrylic resin is in the range of 2.3:1 to 4:1.

(5) A packaged adhesive bandage comprising: the package material for adhesive bandage described in the above-mentioned item (1) and an adhesive bandage packaged in the package material for adhesive bandage, the adhesive bandage including a surface base having one surface, an adhesive layer provided on the one surface of the surface base and a releasing sheet attached to the adhesive layer so as to cover it.

(6) In the packaged adhesive bandage described in the above-mentioned item (5), the surface base of the adhesive bandage is formed from a polyurethane film.

(7) In the packaged adhesive bandage described in the above-mentioned item (5), the adhesive bandage further includes a printed layer provided on the surface base on a side opposite to the adhesive layer.

According to the present invention, it is possible to provide a package material for adhesive bandage in which an adhesive bandage can be packaged in a high hermetically sealed condition and from which the adhesive bandage can be easily picked out, and a packaged adhesive bandage comprised of the package material and the adhesive bandage packaged in the package material.

DETAILED DESCRIPTION OF THE PREFERRED EMBODIMENTS

Hereinbelow, a description will be made on a package material for adhesive bandage and a packaged adhesive bandage according to the present invention in detail based on a preferred embodiment thereof.

Figure 1:
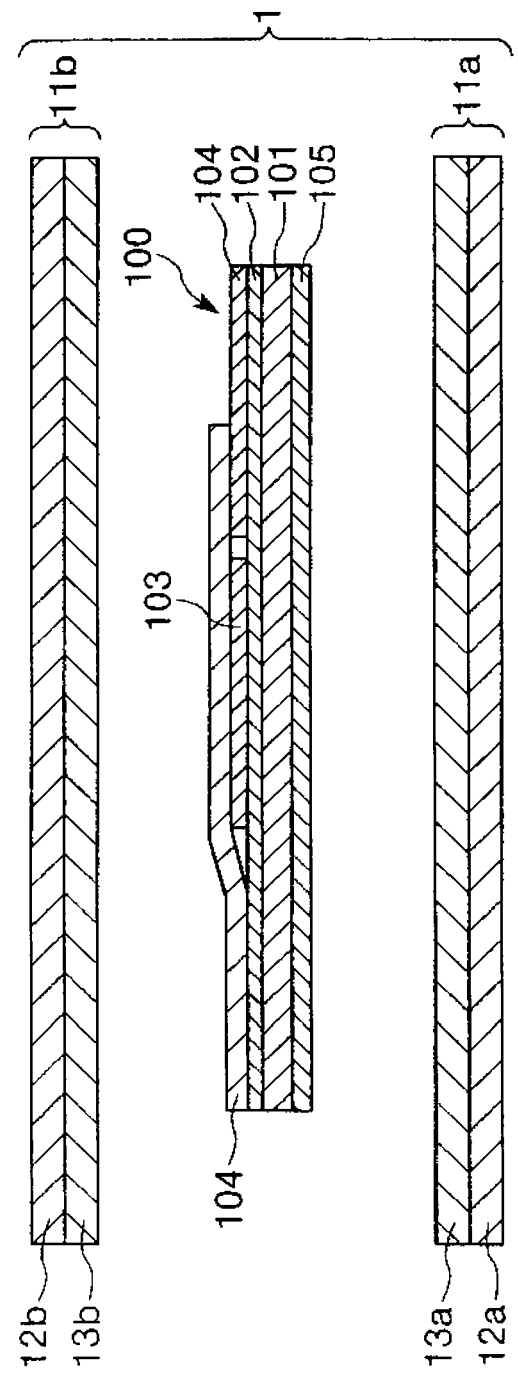
FIG. 1 is a longitudinal cross-sectional view showing a preferred embodiment of a package material for adhesive bandage according to the present invention.
Figure 2:
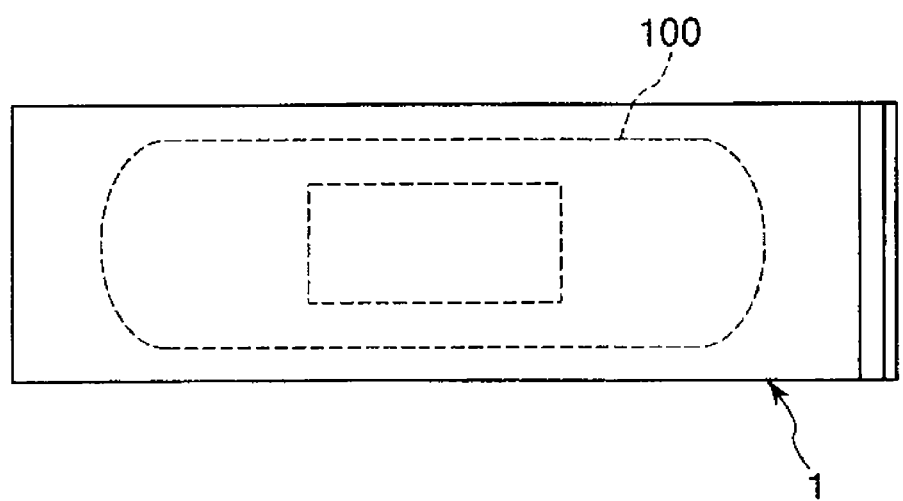
FIG. 2 is a plane view showing a preferred embodiment of a packaged adhesive bandage according to the present invention.

FIG. 1 is a longitudinal cross-sectional view showing a preferred embodiment of the package material for adhesive bandage according to the present invention, and FIG. 2 is a plane view showing a preferred embodiment of the packaged adhesive bandage according to the present invention.

As shown in FIGS. 1 and 2, a package material for adhesive bandage 1 is used for packaging an adhesive bandage 100 therein.

First, a description will be made on the adhesive bandage 100 prior to a description of the package material for adhesive bandage 1.

As shown in FIG. 1, the adhesive bandage 100 includes a surface base 101, an adhesive layer 102 provided on one surface of the surface base 101, a pad layer 103 provided on a surface of the adhesive layer 102 opposite to the surface base 101, a releasing sheet 104 attached to the adhesive layer 102 so as to cover the surface of the adhesive layer 102 on which the pad layer 103 is provided, and a printed layer 105 provided on the other surface of the surface base 101.

The surface base 101 has a function of supporting the adhesive layer 102, the pad layer 103 and the printed layer 105, and is a film mainly formed of a resin material.

Examples of the surface base 101 include a film having flexibility such as a polyurethane film, a vinyl chloride film or a polyolefin film. Among them, it is preferable to use the polyurethane film. This is because the polyurethane film has superior printability and high following capability with respect to a curved surface.

However, in the case where the polyurethane film is used as the surface base 101 of the adhesive bandage 100, there is remarkably a problem in that the surface base 101 is bonded to a package material for adhesive bandage as described below. In contrast, according to the package material for adhesive bandage 1 according to the present invention, even if the polyurethane film is used as the surface base 101, it is possible to effectively prevent occurrence of the above problem.

The adhesive layer 102 is a layer having a function of attaching the adhesive bandage 100 to an affected part of a body.

Examples of a material constituting the adhesive layer 102 include, but are not limited to, acryl-based adhesives, silicone-based adhesives, urethane-based adhesives, natural rubber, and the like.

The pad layer 103 is a layer having functions of stopping loss of blood and protecting the affected part and the like, when the adhesive bandage 100 is attached to the affected part.

As for the pad layer 103, it is possible to use, for example, a woven or nonwoven fabric, a polymer gel including water or oily components, and the like. Further, examples of a constituent material of the woven or unwoven fabric include rayon, polyolefin such as polyethylene or polypropylene, alginate, and the like. These materials may be used singly or in combination of two or more of them.

The releasing sheet 104 has a function of protecting the adhesive layer 102 and the pad layer 103.

As for the releasing sheet 104, it is not particularly limited, but known releasing sheets can be used. Among them, it is preferable to use a releasing sheet having a high surface roughness on a surface thereof which is made contact with a cold seal layer which will be described later as the releasing sheet 104. Particularly, it is more preferable to use a releasing sheet obtained by applying a releasing agent to a paper material. This is because such a releasing sheet has a low bonding property to the cold seal layer.

The printed layer 105 is provided on the surface base 101. For example, in the case of an adhesive bandage for children, the printed layer 105 is a layer for showing a design such as characters. In the case where the printed layer 105 is provided on the surface base 101, the surface base 101 has need to have a low surface roughness on a surface thereof which is made contact with the printed layer 105, in order to make finish of the printed layer 105 beautiful.

However, in the case where the printed layer 105 is provided on the surface base 101 like this embodiment, there is remarkably a problem in that the printed layer 105 is bonded to a package material for adhesive bandage as described below. In contrast, according to the package material for adhesive bandage 1 of the present invention, even if the printed layer 105 is provided on the surface base 101, it is possible to effectively prevent occurrence of the above problem.

Next, a description will be made on the package material for adhesive bandage 1.

As shown in FIG. 1, the package material for adhesive bandage 1 is composed of a first sheet 11a to be placed on a side of the surface base 101 of the adhesive bandage 100, and a second sheet 11b to be placed on a side of the releasing sheet 104 of the adhesive bandage 100.

The first sheet 11a has a sheet base 12a and a cold seal layer 13a provided on the sheet base 12a, and is placed so that the cold seal layer 13a faces the adhesive bandage 100 in a state that the adhesive bandage 100 is packaged in the package material for adhesive bandage 1.

Further, the second sheet 11b has a sheet base 12b and a cold seal layer 13b provided on the sheet base 12b, and is placed so that the cold seal layer 13b faces the adhesive bandage 100 in the state that the adhesive bandage 100 is packaged in the package material for adhesive bandage 1.

Each of the sheet base 12a and the sheet base 12b has a function of supporting the corresponding cold seal layer, and also has a function of preventing the adhesive bandage 100 from being polluted with bacteria and the like in the state that the adhesive bandage 100 is packaged in the package material for adhesive bandage 1.

Examples of each of the sheet base 12a and the sheet base 12b include, but are not limited to, a glassine paper, a high density polyethylene nonwoven fabric, a polyolefin film, a polyester film, and the like. Among them, it is preferable to use the glassine paper. This is because the glassine paper has high permeability of ethylene oxide gas which is used for sterilizing process of the adhesive bandage 100, a superior handling property (e.g., an appropriate bending property) and a low cost.

A basis weight (mass per unit area) of each of the sheet base 12a and the sheet base 12b is preferably in the range of 20 to 300 g/m$^2$, and more preferably in the range of 20 to 50 g/m$^2$.

Each of the cold seal layer 13a and the cold seal layer 13b is a layer having a pressure-sensitive bonding property to be developed when pressure is applied thereto.

Each of the cold seal layer 13a and the cold seal layer 13b is a layer formed of a cold seal agent constituted from rubber and acrylic resin. Since each of the cold seal layer 13a and the cold seal layer 13b contains the rubber as a constituent component thereof, it can develop the pressure-sensitive bonding property.

Such a package material for adhesive bandage 1 can hermetically seal the adhesive bandage 100 therein by placing the first sheet 11a and the second sheet 11b so that the cold seal layer 13a faces the cold seal layer 13b through the adhesive bandage 100 as shown in FIG. 1, and then bonding the cold seal layer 13a to the cold seal layer 13b at an edge portion thereof.

Meanwhile, in a conventional package material formed from a pair of sheets between which an adhesive bandage is packaged by bonding them together at edge portions thereof, sheets having the same configurations are used as the sheet placed on a side of a surface base of the adhesive bandage and the sheet placed on a side of a releasing sheet thereof. In the case where such a conventional package material is stored for a long period of time in a state that an adhesive bandage is packaged therein, there is a problem in that a cold seal layer of the sheet placed on a side of the surface base closely adheres (is bonded) to the surface base over time so that it becomes difficult to separate the adhesive bandage from the package material.

Particularly, in the case where a polyurethane film is used as the surface base or a printed layer is formed on the surface base, the above problem becomes more remarkable. In order to solve the above problem, it may be conceived to provide no cold seal layer in the sheet placed on the side of the surface base. However, in such a case, the adhesive bandage is packaged in the package material in a state that the cold seal layer of the sheet placed on the side of the releasing sheet is bonded to the sheet base of the sheet placed on the side of the surface base. This causes another problem in that a sealing property of the package material cannot be kept. If such a sealing property of the package material is lowered, bacteria and the like infiltrate into the package material from a part thereof incompletely sealed so that the adhesive bandage is polluted. Namely, it is impossible to ensure a sterile condition of the adhesive bandage.

In contrast, the present inventors have intensively studied on the above problem, and as a result have found that an amount of the rubber contained in the cold seal layer of each sheet effects on a bonding property of one of the cold seal layers to the other cold seal layer and a bonding property (adhesion) of the cold seal layer to the surface base of the adhesive bandage, to thereby complete the present invention. Namely, the present inventors have found that the above problem can be solved by setting an amount of the rubber contained in the cold seal layer 13a of the first sheet 11a placed on the side of the surface base 101 of the adhesive bandage 100 so as to become smaller than an amount of the rubber contained in the cold seal layer 13b of the second sheet 11b placed on the side of the releasing sheet 104 of the adhesive bandage 100.

In other words, the package material for adhesive bandage 1 according to the present invention is characterized in that the amount of the rubber contained in the cold seal layer 13a of the first sheet 11a is smaller than the amount of the rubber contained in the cold seal layer 13b of the second sheet 11b. This makes it possible to make the bonding property of the first sheet 11a to the second sheet 11b excellent, to thereby package the adhesive bandage 100 in the package material for adhesive bandage 1 in a high hermetically sealed condition.

Further, even if the package material for adhesive bandage 1 is stored for a long period of time in a state that an adhesive bandage is packaged therein, it is possible to effectively prevent the adhesive bandage 100 from being unable to be separated from the package material for adhesive bandage 1, which would occur due to the bonding of the surface base 101 of the adhesive bandage 100 to the first sheet 11a of the package material for adhesive bandage 1, when being picked out therefrom. As a result, it is possible to easily pick out the adhesive bandage 100 from the package material for adhesive bandage 1.

In the case where the amount of the rubber contained in the cold seal layer 13a of the first sheet 11a is defined as A (mass %) and the amount of the rubber contained in the cold seal layer 13b of the second sheet 11b is defined as B (mass %), A and B preferably satisfy a relation of $1.05 \leq B/A \leq 2.40$, and more preferably a relation of $1.10 \leq B/A \leq 2.30$. By satisfying such a relation, it is possible to package the adhesive bandage 100 in the package material for adhesive bandage 1 in a higher hermetically sealed condition.

Further, it is also possible to more effectively prevent the adhesive bandage 100 from being unable to be separated from the package material for adhesive bandage 1, which would occur due to the bonding of the surface base 101 of the adhesive bandage 100 to the first sheet 11a, when being picked out from the package material for adhesive bandage 1. As a result, it is possible to more easily pick out the adhesive bandage 100 from the package material for adhesive bandage 1.

In the cold seal layer 13a of the first sheet 11a, a mass ratio of the rubber to the acrylic resin is preferably in the range of 0.3:1 to 2.2:1, and more preferably in the range of 1:1 to 1.8:1. This makes it possible to more effectively prevent the adhesive bandage 100 from being unable to be separated from the package material for adhesive bandage 1, which would occur due to the bonding of the surface base 101 of the adhesive bandage 100 to the first sheet 11a, when being picked out from the package material for adhesive bandage 1. Further, it is also possible to package the adhesive bandage 100 in the package material for adhesive bandage 1 in a higher hermetically sealed condition.

In contrast, if the ratio of the rubber contained in the cold seal layer 13a of the first sheet 11a is less than the above lower limited value, there is a case that a sufficient hermetically sealed property of the package material for adhesive bandage 1 cannot be obtained depending on the ratio of the rubber contained in the cold seal layer 13b of the second sheet 11b. On the other hand, if the ratio of the rubber contained in the cold seal layer 13a of the first sheet 11a exceeds the above upper limited value, there is a case that the adhesive bandage 100 cannot be easily and reliably picked out from the package material for adhesive bandage 1 depending on, for example, a constituent material of the surface base 101 of the adhesive bandage 100.

In the cold seal layer 13b of the second sheet 11b, a mass ratio of the rubber to the acrylic resin is preferably in the range of 2.3:1 to 4:1, and more preferably in the range of 2.5:1 to 3.5:1. This makes it possible to package the adhesive bandage 100 in the package material for adhesive bandage 1 in a higher hermetically sealed condition.

In contrast, if the ratio of the rubber contained in the cold seal layer 13b of the second sheet 11b is less than the above lower limited value, there is a case that a sufficient hermetically sealed property of the package material for adhesive bandage 1 cannot be obtained depending on the ratio of the rubber contained in the cold seal layer 13a of the first sheet 11a. On the other hand, if the ratio of the rubber contained in the cold seal layer 13b of the second sheet 11b exceeds the above upper limited value, there is a case that the second sheet 11b becomes sticky, and therefore processability of the package material for adhesive bandage 1 is lowered.

Examples of the rubber contained in the cold seal agent constituting each of the cold seal layer 13a and the cold seal layer 13b include synthetic rubber such as polyisobutylene rubber, polyisoprene rubber, styrene-isoprene-styrene block copolymer, styrene-butadiene copolymer, natural rubber and the like.

In this regard, it is to be noted that a Mooney viscosity ($ML_{1+4}$ (100° C.)) of the above rubber is preferably in the range of 20 to 200, and more preferably in the range of 30 to 150. This makes it possible to further conspicuously exhibit the above effects of the present invention.

Further, as the acrylic resin contained in the cold seal agent constituting each of the cold seal layer 13a and the cold seal layer 13b, (meth)acrylic (co)polymer and the like can be used.

The (meth)acrylic (co)polymer is a polymer obtained by (co)polymerization of a monomer composition including (meth)acrylic acid ester monomer and the other monomer to be arbitrarily added.

Examples of the (meth)acrylic acid ester monomer include (meth)acrylic acid alkyl ester having 1 to 20 carbon atoms in an alkyl group forming the ester portion, such as methyl (meth)acrylate, ethyl (meth)acrylate, n-propyl (meth)acrylate, isopropyl (meth)acrylate, n-butyl (meth)acrylate, isobutyl (meth)acrylate, sec-butyl (meth)acrylate, t-butyl (meth)acrylate, n-pentyl (meth)acrylate, n-hexyl (meth)acrylate, cyclohexyl (meth)acrylate, 2-ethylhexyl (meth)acrylate, isooctyl (meth)acrylate, decyl (meth)acrylate, dodecyl (meth)acrylate, myristyl (meth)acrylate, palmityl (meth)acrylate, stearyl (meth)acrylate, and the like. In this regard, it is to be noted that "(meth)acryl" expresses "acryl" or "methacryl".

These (meth)acrylic acid ester monomers may be used singly or in combination of two or more of them.

Examples of the other monomer include: vinyl esters such as vinyl acetate and vinyl propionate; styrene monomers such as styrene and α-methyl styrene; nitrile monomers such as acrylonitrile and methacrylonitrile; and the like.

As for a method of polymerization of the monomer composition described above, it is not particularly limited, but known methods such as emulsion polymerization and radical polymerization can be used.

An application amount of the cold seal layer $13a$ of the first sheet $11a$ is preferably in the range of 3 to 10 $g/m^2$, and more preferably in the range of 4 to 6 $g/m^2$.

On the other hand, an application amount of the cold seal layer $13b$ of the second sheet $11b$ is preferably in the range of 3 to 10 $g/m^2$, and more preferably in the range of 4 to 6 $g/m^2$.

Although the package material for adhesive bandage and the packaged adhesive bandage according to the present invention have been described with reference to the preferred embodiment thereof, the present invention is not limited thereto.

EXAMPLES

Hereinbelow, actual examples according to the present invention will be described.

(1) Production of Package Material for Adhesive Bandage and Packaged Adhesive Bandage Example 1

Formation of First Sheet

First, a glassine paper (basis weight: 40 $g/m^2$) was prepared as a sheet base, and then an emulsion type cold seal agent (solid content: 30 mass %) containing rubber (natural rubber, a Mooney viscosity ($ML_{1+4}$ (100° C.)): 40) and acrylic resin (ethyl acrylate-methyl methacrylate copolymer) was applied onto the glassine paper so as to become an application amount of 5 $g/m^2$ after being dried. In this regard, in the emulsion type cold seal agent, a mass ratio of the rubber to the acrylic resin was 1.5:1.

Thereafter, the emulsion type cold seal agent was dried by being heated at 100° C. for 5 minutes to form a cold seal layer. In this way, a first sheet was obtained.

Formation of Second Sheet

First, a glassine paper (basis weight: 40 $g/m^2$) was prepared as a sheet base, and then an emulsion type cold seal agent (solid content: 30 mass %) containing rubber (natural rubber, a Mooney viscosity ($ML_{1+4}$ (100° C.)): 40) and acrylic resin (ethyl acrylate-methyl methacrylate copolymer) was applied onto the glassine paper so as to become an application amount of 5 $g/m^2$ after being dried. In this regard, in the emulsion type cold seal agent, a mass ratio of the rubber to the acrylic resin contained was 3:1.

Thereafter, the emulsion type cold seal agent was dried by being heated at 100° C. for 5 minutes to form a cold seal layer. In this way, a second sheet was obtained.

[Production of Packaged Adhesive Bandage]

An adhesive bandage having a printed layer provided on a surface base (configuration: a printed layer with characters as a design/a polyurethane film (surface base) having a thickness of 50 μm/an acryl-based adhesive layer/a pad layer/a releasing layer; size: 19 mm×72 mm) was placed in a package material for adhesive bandage composed of a first sheet and a second sheet, so that the printed layer faced the cold seal layer of the first sheet and the releasing sheet faced the cold seal layer of the second sheet. And then, the adhesive bandage was hermetically sealed in the package material for adhesive bandage by bonding the first sheet to the second sheet at an edge portion thereof by pressure bonding, to thereby obtain a packaged adhesive bandage as shown in FIG. 2.

Examples 2 to 7

A package material for adhesive bandage (first sheet and second sheet) and a packaged adhesive bandage were produced in the same manner as in Example 1 except that the mass ratio of the rubber to the acrylic resin in each of the first sheet and the second sheet was changed as shown in Table 1.

Comparative Examples 1 to 7

A package material for adhesive bandage (first sheet and second sheet) and a packaged adhesive bandage were produced in the same manner as in Example 1 except that the mass ratio of the rubber to the acrylic resin in the first sheet was equal to that in the second sheet, and the mass ratio was set to a value as shown in Table 1.

In each of Examples and Comparative Examples, the mass ratio of the rubber to the acrylic resin, and a value of B/A (where the amount of the rubber contained in the cold seal layer of the first sheet was defined as A (mass %) and the amount of the rubber contained in the cold seal layer of the second sheet was defined as B (mass %)) are shown in Table 1.

TABLE 1

|  | First sheet Rubber: Acrylic resin | Second sheet Rubber: Acrylic resin | B/A |
| --- | --- | --- | --- |
| Ex. 1 | 1.5:1.0 | 3.0:1.0 | 1.25 |
| Ex. 2 | 1.5:1.0 | 2.5:1.0 | 1.19 |
| Ex. 3 | 1.0:1.0 | 3.0:1.0 | 1.50 |
| Ex. 4 | 1.0:1.0 | 2.5:1.0 | 1.43 |
| Ex. 5 | 0.5:1.0 | 3.0:1.0 | 2.25 |
| Ex. 6 | 0.5:1.0 | 2.5:1.0 | 2.14 |
| Ex. 7 | 2.0:1.0 | 2.5:1.0 | 1.07 |
| Com. Ex. 1 | 3.5:1.0 | 3.5:1.0 | 1.00 |
| Com. Ex. 2 | 3.0:1.0 | 3.0:1.0 | 1.00 |
| Com. Ex. 3 | 2.5:1.0 | 2.5:1.0 | 1.00 |
| Com. Ex. 4 | 2.0:1.0 | 2.0:1.0 | 1.00 |

TABLE 1-continued

|  | First sheet<br>Rubber:<br>Acrylic resin | Second sheet<br>Rubber:<br>Acrylic resin | B/A |
|---|---|---|---|
| Com. Ex. 5 | 1.5:1.0 | 1.5:1.0 | 1.00 |
| Com. Ex. 6 | 1.0:1.0 | 1.0:1.0 | 1.00 |
| Com. Ex. 7 | 0.5:1.0 | 0.5:1.0 | 1.00 |

(2) Evaluation (2-1) Difficulty for Picking Out Adhesive Bandage From Package Material for Adhesive Bandage The packaged adhesive bandage obtained in each of Examples and Comparative Examples was stored under the accelerated condition (40° C., 75% RH) for six months.

Next, the second sheet of the package material for adhesive bandage placed on the side of the releasing sheet of the adhesive bandage was peeled-off from the first sheet thereof, and then the releasing sheet of the adhesive bandage was peeled-off from the adhesive layer thereof. Thereafter, a PET film having a thickness of 25 μm and cut so as to have the same width as that of the adhesive bandage was attached to the adhesive layer.

Next, in a state that the PET film was fixed, the first sheet was bent and pulled in a 180° direction at a speed of 300 mm/min. In this way, a tensile stress was measured, and then unit of the measured tensile stress was converted to unit of "N/25 mm".

Further, by carrying out an operation of peeling-off the adhesive bandage from the first sheet by hand, a bonding property of the printed layer to the cold seal layer was evaluated by sensory test based on the following four criteria A to D.

A: The adhesive bandage is easily peeled-off from the first sheet by hand.

B: The adhesive bandage is slightly bonded to the first sheet, but a degree of the bonding is within the acceptable range.

C: The adhesive bandage is firmly bonded to the first sheet.

D: The adhesive bandage is integrated with the first sheet (that is, the adhesive bandage cannot be peeled-off from the first sheet).

(2-2) Hermetically Sealed Property

The packaged adhesive bandage obtained in each of Examples and Comparative Examples was cut into half using a scissors, and then the adhesive bandage was picked out from the package material for adhesive bandage, to thereby obtain a pouched test piece.

Next, a nozzle of a spray was inserted inside the pouched test piece, and then the following test solution was sprayed from the nozzle one or two times. After that, it was confirmed that a whole inner surface of the pouched test piece was wetted.

Thereafter, this condition of the test piece was kept for 30 seconds. At this time, it was confirmed as to whether or not the test solution passes through the bonded edge portion of the test piece. In the case where the test solution does not pass through the bonded edge portion, the hermetically sealed property was defined as "A". On the other hand, in the case where the test solution passes through the bonded edge portion, the hermetically sealed property was defined as "B".

The test solution contains 0.45 g of povidone iodine, 40 g of glycerin, 24 g of propylene glycol, 17 mL of ethanol, 25 g of D-sorbitol (70%) and 0.3 g of potassium iodide.

These results are shown in Table 2.

TABLE 2

|  | Difficulty for picking out adhesive bandage from package material for adhesive bandage | | Hermetically sealed property |
|---|---|---|---|
|  | Tensile stress [N/25 mm] | Bonding property (sensible evaluation) | |
| Ex. 1 | 0.3 | A | A |
| Ex. 2 | 0.3 | A | A |
| Ex. 3 | 0.3 | A | A |
| Ex. 4 | 0.3 | A | A |
| Ex. 5 | 0.2 | A | A |
| Ex. 6 | 0.2 | A | A |
| Ex. 7 | 0.5 | B | A |
| Com. Ex. 1 | 1.7 (Destruction of sheet base) | D | A |
| Com. Ex. 2 | 1.6 (Destruction of sheet base) | D | A |
| Com. Ex. 3 | 1.2 | D | A |
| Com. Ex. 4 | 0.5 | B | B |
| Com. Ex. 5 | 0.3 | A | B |
| Com. Ex. 6 | 0.3 | A | B |
| Com. Ex. 7 | 0.2 | A | B |

As can be seen from Table 2, in the package material for adhesive bandage (packaged adhesive bandage) according to the present invention, the adhesive bandage is sealed therein in a high hermetically sealed property, and the adhesive bandage can be easily picked out therefrom. On the other hand, in Comparative Examples, satisfactory results cannot be obtained.

EXPLANATION OF REFERENCE NUMERAL

1 . . . package material for adhesive bandage
11a . . . first sheet
11b . . . second sheet
12a, 12b . . . sheet base
13a, 13b . . . cold seal layer
100 . . . adhesive bandage
101 . . . surface base
102 . . . adhesive layer
103 . . . pad layer
104 . . . releasing sheet
105 . . . printed layer

What is claimed is:

1. A package material for an adhesive bandage which is adapted to be used for packaging an adhesive bandage therein, the adhesive bandage including a surface base having one surface, an adhesive layer provided on the one surface of the surface base and a releasing sheet attached to the adhesive layer so as to cover it, the package material for adhesive bandage comprising:

a first sheet having a first sheet base and a first cold seal layer provided on the first sheet base; and a second sheet having a second sheet base and a second cold seal layer provided on the second sheet base, wherein the first cold seal layer faces the surface base of the adhesive bandage and the second cold seal layer faces the releasing sheet of the adhesive bandage when the adhesive bandage is packaged in the package material for adhesive bandage, wherein each of the first sheet base and the second sheet base is a glassine paper, wherein each of the first cold seal layer and the second cold seal layer is formed of a mixture of rubber and acrylic resin, wherein in the first cold seal layer, a mass ratio of the rubber to the acrylic resin is in the range of 0.3:1 to 2.2:1, wherein in the second cold seal layer, a mass ratio of the rubber to the acrylic resin is in the range of 2.3:1 to 4:1 wherein the acrylic resin is a (meth)acrylic (co)polymer obtained by (co)polymerizing a (meth)acrylic acid ester monomer, wherein the (meth)acrylic acid ester monomer is a (meth)acrylic acid alkyl ester having 1 to 20 carbon atoms in an alkyl group forming an ester portion thereof, wherein an amount of the rubber contained in the first cold seal layer is smaller than an amount of the rubber contained in the second cold seal layer and wherein in the case where the amount of the rubber contained in the first cold seal layer is defined as A (mass %) and the amount of the rubber contained in the second cold seal layer is defined as B (mass %), A and B satisfy a relation of $1.05 \leq B/A \leq 2.40$.

2. The package material for the adhesive bandage as claimed in claim 1, wherein in the case where the amount of the rubber contained in the first cold seal layer is defined as A (mass %) and the amount of the rubber contained in the second cold seal layer is defined as B (mass %), A and B satisfy a relation of $1.10 \leq B/A \leq 2.30$.

3. The package material for the adhesive bandage as claimed in claim 1, wherein in the first cold seal layer, a mass ratio of the rubber to the acrylic resin is in the range of 1:1 to 1.8:1.

4. The package material for the adhesive bandage as claimed in claim 1, wherein in the second cold seal layer, a mass ratio of the rubber to the acrylic resin is in the range of 2.5:1 to 3.5:1.

5. A packaged adhesive bandage comprising:
the package material for the adhesive bandage defined by claim 1; and
an adhesive bandage packaged in the package material for adhesive bandage, the adhesive bandage including a surface base having one surface, an adhesive layer provided on the one surface of the surface base and a releasing sheet attached to the adhesive layer so as to cover it.

6. The packaged adhesive bandage as claimed in claim 5, wherein the surface base of the adhesive bandage is formed from a polyurethane film.

7. The packaged adhesive bandage as claimed in claim 5, wherein the adhesive bandage further includes a printed layer provided on the surface base on a side opposite to the adhesive layer.

8. The package material for the adhesive bandage as claimed in claim 1, wherein the acrylic resin is an ethyl acrylate-methyl methacrylate copolymer.

9. The package material for the adhesive bandage as claimed in claim 1, wherein a Mooney viscosity ($ML_{1+4}$ (100° C.)) of the rubber is in the range of 20 to 200.

10. The package material for the adhesive bandage as claimed in claim 1, wherein an application amount of the first cold seal layer of the first sheet is in the range of 3 to 10 $g/m^2$, and wherein an application amount of the second cold seal layer of the second sheet is in the range of 3 to 10 $g/m^2$.

11. The package material for the adhesive bandage as claimed in claim 1, wherein a basis weight (mass per unit area) of the first sheet base is in the range of 20 to 300 $g/m^2$, and wherein a basis weight (mass per unit area) of the second sheet base is in the range of 20 to 300 $g/m^2$.

12. The package material for the adhesive bandage as claimed in claim 1, wherein each of the rubber contained in the first cold seal layer and the rubber contained in the second cold seal layer is one selected from the group consisting of a polyisobutylene rubber, a polyisoprene rubber, a styrene-isoprene-styrene block copolymer, a styrene-butadiene copolymer and a natural rubber.

13. The package material for the adhesive bandage as claimed in claim 1, wherein the adhesive bandage further includes a pad layer provided on one surface of the adhesive layer opposite to the surface base, and wherein the releasing sheet is attached to the one surface of the adhesive layer so as to cover the one surface of the adhesive layer on which the pad layer is provided.

* * * * *